(12) United States Patent
Rey et al.

(10) Patent No.: US 7,138,523 B2
(45) Date of Patent: Nov. 21, 2006

(54) PREPARATION OF 4-(4-FLUOROPHENYL)-N-ALKYLNIPECOTINATE ESTERS, 4-(4-FLUOROPHENYL)-N-ARYLNIPECOTINATE ESTERS AND 4-(4-FLUOROPHENYL)-N-ARALKYLNIPECOTINATE ESTERS

(75) Inventors: Allan W. Rey, Brantford (CA); K. S. Keshava Murthy, Ancaster (CA); Bruno K. Radatus, Brantford (CA); Yajun Zhao, Brantford (CA); Tania E. Nish, Brantford (CA)

(73) Assignee: Apotex Pharmachem Inc., Brantford (CA)

( * ) Notice: Subject to any disclaimer, the term of this patent is extended or adjusted under 35 U.S.C. 154(b) by 0 days.

(21) Appl. No.: 10/147,034

(22) Filed: May 17, 2002

(65) Prior Publication Data
US 2003/0220370 A1 Nov. 27, 2003

(30) Foreign Application Priority Data
May 16, 2002 (CA) .................................... 2386981

(51) Int. Cl.
C07D 211/60 (2006.01)
(52) U.S. Cl. ........................................ 546/197; 514/321
(58) Field of Classification Search ................ 514/321; 546/197; 260/665 G
See application file for complete search history.

(56) References Cited

U.S. PATENT DOCUMENTS

| 2,546,652 A | 3/1951 | Plati et al. ................... 546/111 |
| 3,912,743 A | 10/1975 | Christensen et al. ........ 546/197 |
| 4,007,196 A | 2/1977 | Christensen et al. ........ 546/197 |
| 5,672,612 A * | 9/1997 | Ronsen et al. ............... 514/338 |
| 5,872,132 A * | 2/1999 | Ward et al. .................. 514/321 |
| 5,962,689 A | 10/1999 | Murthy et al. ............... 546/185 |
| 6,172,233 B1 | 1/2001 | Ward ........................... 546/185 |
| 6,436,956 B1 * | 8/2002 | Murthy et al. ............... 514/321 |

FOREIGN PATENT DOCUMENTS

| WO | WO 01/17966 A1 | 3/2001 |
| WO | WO 01/29032 A1 | 4/2001 |

OTHER PUBLICATIONS

Lundback "Preparation of 3-hydroxy . . . " CA 114:6300 (1991).*
Blanco et al. "Chiral sulfinic acids . . . " CA 122:160133 (1995).*
Engelstoft et al. "Wynthesis and 5HT modulating . . . " CA 125:10566 (1996).*
Japan chemical society, v.18, p. 504-505 (1957).*
Boudin et al. "Gringnard . . . " CA 111:134232 (1989).*
Mitsui et al. "Method for manufacturing . . . " CA 132:279347 (2000).*
Englestoft, M. et al., "Synthesis and 5HT Modulating Activity of Stereoisomers of 3-Phenoxymethyl-4-phenylpiperidines", Acta Chemica Scandinavica, 50 (1996), pp. 164-169.
Plati, J. et al., "Pyridindene Derivatives. III. Synthesis from Arecoline", Journal of Organic Chemistry, 22 (1957), pp. 261-265.
Xu, L. et al., "Stereoselective Synthesis of 2β-Carbomethoxy-3β-phenyltropane Derivatives. Enhanced Stereoselectivity Observed for the Conjugate Addition Reaction of Phenylmagnesium Bromide Derivatives with Anhydro Dichloromethane", J. Heterocyclic Chem., 33 (1996), pp. 2037-2039.

* cited by examiner

Primary Examiner—Celia Chang
(74) Attorney, Agent, or Firm—Ivor M. Hughes; Neil H. Hughes; Marcelo K. Sarkis

(57) ABSTRACT

A process for the industrial scale manufacture of 4-(4-fluorophenyl)-N-alkylnipecotinate esters by the addition of 4-fluorophenylmagnesium halide in tetrahydrofuran to 3,4-unsaturated-3-piperidine esters.

21 Claims, No Drawings

PREPARATION OF 4-(4-FLUOROPHENYL)-N-ALKYLNIPECOTINATE ESTERS, 4-(4-FLUOROPHENYL)-N-ARYLNIPECOTINATE ESTERS AND 4-(4-FLUOROPHENYL)-N-ARALKYLNIPECOTINATE ESTERS

Preparation of 4-(4-fluorophenyl)-N-alkylnipecotinate esters, 4-(4-fluorophenyl)-N-arylnipecotinate esters and 4-(4-fluorophenyl)-N-aralkylnipecotinate esters.

BACKGROUND OF THE INVENTION 4-(4-Fluorophenyl)-N-alkylnipecotinate esters of general formula A represent key intermediates in the synthesis of 4-arylpiperidine-based compounds. It is noteworthy that 4-arylpiperidine is an important structural motif in many biologically active compounds (M. Engelstoft and J. B. Hansen, Acta Chemical Scandinavica, 50, 1996, pp. 164–169).

A

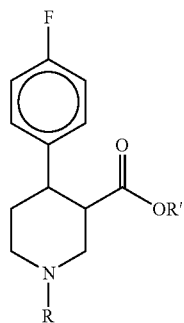

An example is (−)-menthyl (3S,4R)-trans-4-(4-fluorophenyl)-N-methylnipecotinate hydrobromide (1) which is a key intermediate in the synthesis of paroxetine. Paroxetine (Paxil®) is a highly effective chiral pharmaceutical that is useful for the treatment of depression and obsessive compulsive disorder.

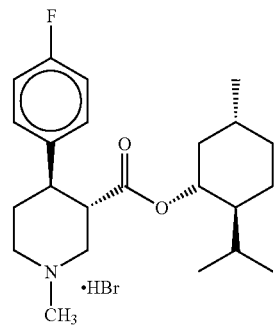

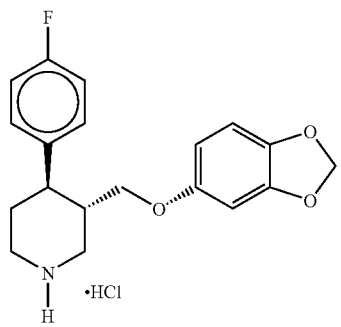

Paroxetine (Paxil™)

The use of this compound for this purpose was disclosed in U.S. Pat. Nos. 3,912,743 and 4,007,196 whereby 4-fluorophenylmagnesium bromide was added to arecoline. The resulting adduct was epimerized and the methyl ester functionality hydrolyzed, activated using thionyl chloride, esterified using (−)-menthol, and salt formation using hydrobromic acid to provide compound 1, as depicted in Scheme 1, which was further elaborated to paroxetine using standard procedures.

SCHEME 1

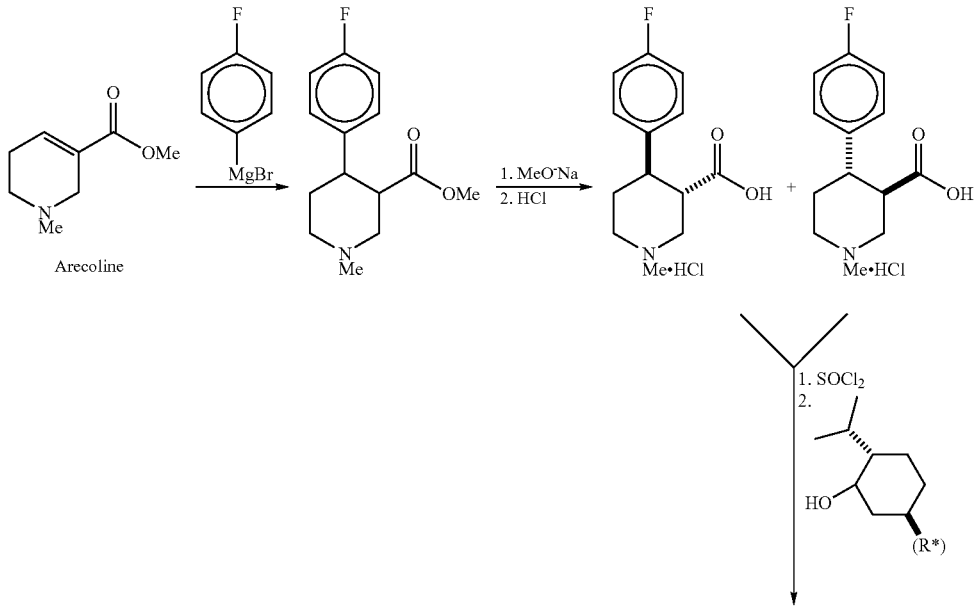

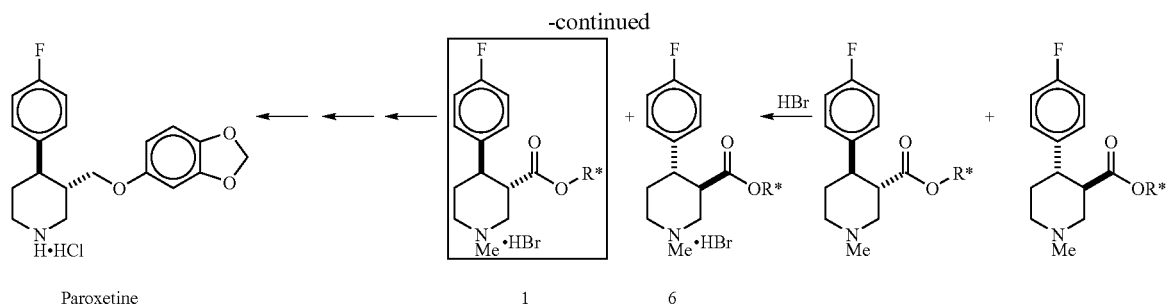

Paroxetine

The procedure disclosed in these patents for the key Grignard conjugate addition step was based on a procedure developed by Plati et al. (U.S. Pat. No. 2,546,652 and Journal of Organic Chemistry, 22, 1957, pp. 261–265) for the reaction of phenylmagnesium bromide in diethyl ether with arecoline, also in diethyl ether. Thus, a major deficiency of this process, and likewise the processes disclosed in U.S. Pat. Nos. 3,912,743 and 4,007,196, was the diethyl ether in both the arylmagnesium bromide reagent and the reaction media. Diethyl ether is a highly flammable solvent which is undesirable to use industrially. According to patents by Ward [(U.S. Pat. No. 6,172,233) and Ward et al. (WO 01/17966A1 and WO 01/29032A1)], the use of other ether solvents conventionally used in Grignard reactions, such as tetrahydrofuran (THF) or diisopropyl ether, furnished little, if any, of the desired 1,4-conjugate addition product, with the main by-product arising from 1,2-addition of the Grignard reagent on the ester grouping. From an industrial perspective, a multistep transformation in which one step resulted in, "little if any of the desired product" (for instance <10% yield) would be prohibitively expensive. Compounding this deficiency, if this process were to be used for the synthesis of paroxetine, is the fact that the low yielding step occurs at a rather late-stage in the paroxetine process, thereby necessitating the processing of large volumes of intermediary products in order to reach the Grignard reaction step. Also, disclosed in the Ward patent was the observation that when performing the reaction using the process described by Plati et al., the reaction mixture purportedly generated thick unstirrable gels.

These deficiencies were purportedly overcome by Ward by the use of a reaction solvent mixture which was non-wholly ether, as utilized by Plati et al. As well, the Ward patents purport that the use of organometallic compounds in place of the Grignard reagent also overcame these deficiencies. However, in all examples in the Ward patents, the Grignard reagent used was always a 2M solution of 4-fluorophenylmagnesium bromide in diethyl ether. Specifically, in examples 2, 3, 4 and 5 of U.S. Pat. No. 6,172,233, the weight percentage of diethyl ether introduced by the 4-fluorophenylmagnesium bromide in diethyl ether reagent relative to the total reaction volume was about 23 to 31% range. Therefore the disadvantage of having a process which necessitated diethyl ether, with all of the disadvantages associated with this solvent, largely remained. In example 1 of the same patent, the diethyl ether is removed from the 2M 4-fluorophenylmagnesium bromide reagent prior to the addition to arecoline by co-distillation with toluene. However, this requires an extra process operation and, again, does not avoid the use of diethyl ether on an industrial scale.

Similar reactions have also been utilized for transformations of this type. For instance, Murthy and Rey in U.S. Pat. No. 5,962,689 disclose the stereoselective addition of 4-fluorophenylmagnesium bromide to various 3,4-unsaturated-3-piperidine esters, amides and N-enoylsultams in toluene. Xu and Trudell (J. Heterocyclic Chem., 33, 1996, pp. 2037–2039) also described the addition of various arylmagnesium bromide reagents, including 4-fluorophenylmagnesium bromide, to R-(−)-anhydroecgonine methyl ester substrates in dichloromethane. The disadvantage in both of these publications is that a solution of the aryl Grignard reagent in diethyl ether was employed.

It is therefore an object of the invention to provide a process which utilizes solvents other than diethyl ether to arrive at yields greater than "little if any" of the desired product.

It is therefore also another object of the invention to provide a process that is easy to perform and incorporates solvents that are less flammable and/or less toxic relative to solvents used as reaction media in the prior art.

It is also an object of the invention to provide a process which results in substantially no gels being formed, even on scale up to industrial quantities.

Further and other objects of the invention will become apparent to a person reading the following.

SUMMARY OF THE INVENTION

To overcome these difficulties, we sought an alternative method whereby the aryl Grignard reagent in a solvent which was not diethyl ether could be used for the conjugate addition to an arecoline based substrate 2 (Scheme 2). Surprisingly, we discovered that using the 4-fluorophenylmagnesium bromide reagent in THF, contrary to the teachings of the Ward patent, resulted in clean 1,4-conjugate addition when dibutyl ether was used as the reaction media producing about in one instance a 50–90% (which is at least greater than about 10% of a more than "little if any") molar yield of the desired adduct 3. Surprisingly, none of the 1,2-byproduct was noted but rather the 4,5-isomer 4 (7–15%). Only a trace amount of product arising from 1,2-addition was noted, namely the 1,2:1,4-compound 5. The Ward patents teach away from the use of a solvent other than diethyl ether since Ward reported "little if any" desired product. Furthermore, it appears that Ward did not carry out the processes, since in carrying out the process using solvents other than diethyl ether we arrive at results in yield substantially more than "little if any" of the desired product.

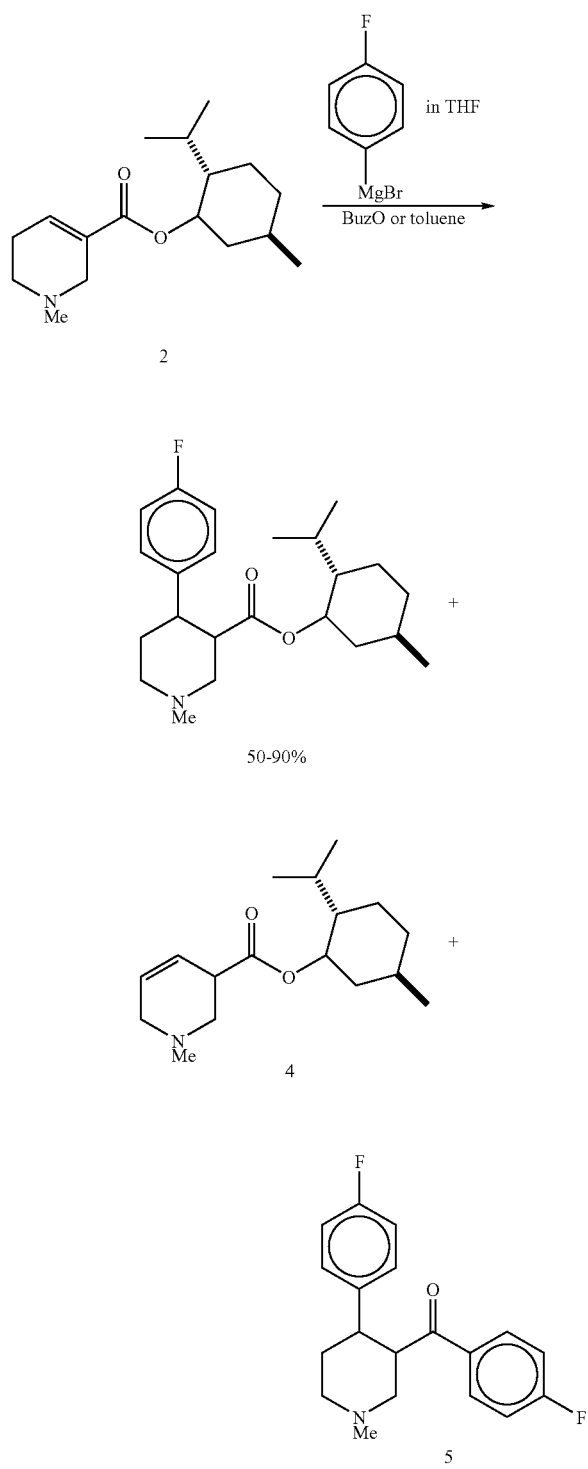

SCHEME 2

For this type of reaction, there are several beneficial features of using 4-fluorophenylmagnesium bromide in a suitable reagent, such as a THF reagent and in a suitable reaction media, such as dibutyl ether as the reaction media. The beneficial features include, but are not limited to, substantially no gels are formed, even on scale-up to industrial quantities. Also in terms of industrial applicability, the suitable reaction media, such as dibutyl ether is less flammable and/or toxic relative to diethyl ether, toluene and dichloromethane which were used as the reaction media in the prior art. This is due to the reduced volatility of dibutyl ether (bp=142–143° C.) relative to the other solvents. Another industrial advantage is that it is substantially facile to perform the reaction under substantially if not completely anhydrous conditions by azeotropically removing water by distilling a small amount of the dibutyl ether solvent from the reaction mixture. This avoids the necessity of pre-drying the solvent using drying reagents such as metallic sodium or calcium oxide. Finally, the high boiling point of dibutyl ether facilitates solvent recovery which represents an industrially important advantage since it minimizes costs by solvent recycling and waste reduction. Methods for the preparation of the (1R,2S,5R)-(−)-menthyl arecoline substrate 2 and other substrates of this type are described in U.S. Pat. No. 5,962,689 by Murthy and Rey.

In general, the conjugate addition reaction may be performed using 4-fluorophenylmagnesium bromide Grignard reagent preferably in THF preferably at a stoichiometry of 1.0 to 2.0 equivalents relative to the arecoline-based substrate, more preferably at 1.1 to 1.5 equivalents and most preferably at 1.2 to 1.4 equivalents. The reaction may be performed in an organic solvent such as a hydrocarbon (aliphatic and aromatic), halogenated hydrocarbon, or ether. Preferably suitable solvents include toluene, heptanes, dibutyl ether, methyl tert-butyl ether, isopropyl ether, tetrahydrofuran or mixtures thereof. More preferable solvents include dibutyl ether, tetrahydrofuran or toluene. The most preferred solvent is dibutyl ether. The reaction is preferably carried out under an inert atmosphere, for example under argon or nitrogen. The reaction may be conducted at a temperature of preferably −10° C. to 50° C., more preferably at −10° to 30° C., and most preferably at −10° to 20° C. Under these conditions, the reaction is complete in less than about 8 hours. If desired, a copper species may be added to the reaction mixture such as cuprous chloride, cuprous bromide, cuprous iodide, or cuprous bromide-dimethyl sulfide complex. The use of 4-fluorophenylmagnesium chloride in diethyl ether may also be used as the Grignard source.

The conjugate addition product 3 (Scheme 2) was further elaborated to 1 by epimerization to the thermodynamically more stable trans-geometry at the C-3 and C-4 position of the piperidine ring using potassium tert-butoxide followed by salt formation using 48% hydrobromic acid. The stereoisomer requisite for further elaboration to paroxetine, (−)-menthyl (3S,4R)-trans-4-(4-fluorophenyl)-N-methylnipecotinate hydrobromide (1), precipitated from the reaction mixture and was isolated by filtration. The menthyl (3R,4S)-trans-4-(4-fluorophenyl)-N-methylnipecotinate hydrobromide (6) stereoisomer remained in the filtrate. These transformations are described in the examples 1 to 8.

In another aspect of the invention, we were surprisingly able to isolate in high purity and yield and as a crystalline solid the stereoisomer menthyl (3R,4S)-trans-4-(4-fluorophenyl)-N-methylnipecotinate hydrobromide (6) by concentration of the filtrate after the precipitation of 1. This compound may be of use for either conversion to (−)-menthyl (3S,4R)-trans-4-(4-fluorophenyl)-N-methylnipecotinate hydrobromide by epimerization of the stereocentres at C-3 and C-4 of the piperidine ring or for producing the (3R,4S)-enantiomer of paroxetine.

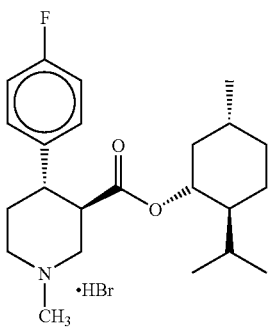

In another aspect of the invention, a cost effective, safe and scalable method for the synthesis exemplified by (−)-menthyl (3S,4R)-trans-4-(4-fluorophenyl)-N-methylnipecotinate hydrobromide (1) has been discovered using 4-fluorophenylmagnesium bromide in THF and, most preferably, where the reaction is performed in a wholly ether reaction media. This method avoids the deficiencies of the prior art where diethyl ether was used either as part of the Grignard reagent or as reaction media. The compound 1 represents a key intermediate in the synthesis of the medicinally valuable antidepressant paroxetine. Also, this route permits the isolation of 6 which can be further elaborated to (+)-(3R,4S)-trans-3-[(1,3-Benzodioxol-5-yloxy)methyl]-4-(4-fluorophenyl)piperidine hydrochloride, or else recycled to 1.

Thus, according to one aspect of the invention, there is provided a process for the industrial scale preparation of a compound of structure A or salts thereof

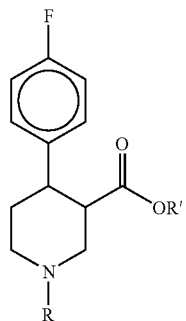

A in which R and R' are selected from an alkyl, cycloalkyl (such as (1R,2S,5R)-(−)-menthyl), aryl, or aralkyl group, which comprises reacting a compound of structure B

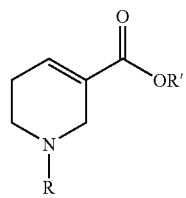

B with an organometallic compound of structure C, in a suitable organic solvent with the proviso that it is not diethyl ether

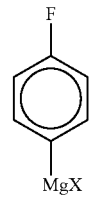

C where X is Cl or Br. Preferably the suitable organic solvent is selected from the group consisting of dibutyl ether, tetrahydrofuran, or toluene.

In one embodiment, R is methyl and R' is (1R,2S,5R)-(−)-menthyl. Preferably, the salt form of A is HBr.

In another embodiment, the yield of A is greater than "little if any" product, preferably greater than 10%, preferably yet 50% or greater.

In yet another embodiment, as part of the invention, there is provided a process for the preparation of 1 according to the procedure described herein.

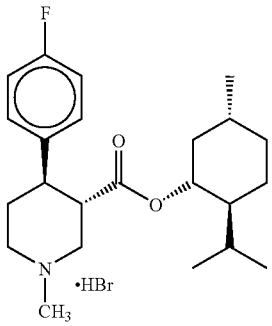

1

In another embodiment, 1 is further converted to paroxetine hydrochloride.

In yet another embodiment, there is provided a process for the preparation and isolation of 6 according to the procedures described herein.

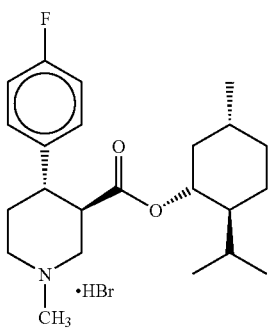

6

Preferably, 6 is further converted to (+)-(3R,4S)-trans-3-[(1,3-Benzodioxol-5-yloxy)methyl]-4-(4-fluorophenyl)piperidine hydrochloride.

In another aspect of the invention, there is provided menthyl (3R,4S)-trans-4-(4-fluorophenyl)-N-methylnipecotinate hydrobromide in crystalline form.

In another aspect of the invention, there is provided (+)-(3R,4S)-trans-3-[(1,3-Benzodioxol-5-yloxy)methyl]-4-(4-fluorophenyl)piperidine hydrochloride.

The following examples are illustrative of the invention and are not to be construed as limiting the scope of the invention in any manner.

EXAMPLE 1

Preparation of (−)-menthyl (3S,4R)-trans-4-(4-fluorophenyl)-N-methylnipecotinate hydrobromide (1) in dibutyl ether (DBE)

A round bottom flask was charged with 4-fluorophenylmagnesium bromide (1M in THF, 140 mL, 0.140 mol) and the flask was cooled to −10 to −8° C. and kept under a nitrogen atmosphere. To this mixture was added (1R,2S,5R)-(−)-menthyl arecoline (28.0 g, 0.100 mol) in DBE (total volume of solution=160 mL) over a period of about 1 hour. The solution was warmed to 12 to 16° C. and the reaction was kept at this temperature a further 4 hours. It was then cooled to −5 to −10° C. and saturated aqueous ammonium chloride (158 mL) was added while maintaining the temperature below 10° C. The mixture was filtered through a Celite pad and the filter cake washed with DBE (2×31 mL) and the filtrate was transferred to a separatory funnel. The aqueous layer was removed and back-extracted with DBE (31 mL). The combined organic layers were concentrated to 160 mL. A HPLC assay at this point indicated 33.5 g of (cis/trans)-menthyl-4-(4-fluorophenyl)-N-methylnipecotinate (89% yield from (1R,2S,5R)-(−)-menthyl arecoline). The solution was cooled to −5° C. whereupon potassium tert-butoxide (5.6 g, 0.050 mol, 0.5 eq) was added in portions over a 0.5 to 1 hour period. The reaction mixture was then stirred at 0° C. until reaction completion. The pH was adjusted to 8–9 using 0.7 M HCl and the reaction mixture transferred to a separatory funnel and the layers were separated. The aqueous layer was back-extracted with DBE (62 mL) and the organic layers were combined and concentrated to 160 mL. This solution was cooled to −5° C. and 48% aqueous hydrobromic acid was added (11.3 mL, 0.10 mol) over about 0.5 hours. The reaction mixture was charged with ethyl acetate (188 mL) and stirred at 0° C. for a further 1.5 hours. The precipitated product was collected by filtration and the filter cake was rinsed with a portion of ethyl acetate and the solid dried a 40 to 45° C. in vacuo. This provided 15.08 g (33% yield from (1R,2S,5R)-(−)-menthyl arecoline) of the (−)-menthyl (3S,4R)-trans-4-(4-fluorophenyl)-N-methylnipecotinate hydrobromide as a white solid. $^1$H NMR (DMSO) δ: 9.71 (1H, br.s), 7.14–7.24 (4H, m), 4.37 (1H, atd, J=4.2, 10.8 Hz), 3.70 (1H, ad, J=10.4 Hz), 3.52 (1H, ad, J=11.8 Hz), 3.13–3.19 (3H, m), 2.94–3.05 (1H, m), 2.86 (3H, s), 1.90–2.15 (m, 2H), 1.69 (1H, ad J=11.5 Hz), 1.52–1.62 (1H, m), 1.43–1.51 (1H, m), 1.25–1.42 (1H, br.m), 1.02–1.13 (1H, m), 0.80–0.92 (1H, m), 0.75–0.90 (1H, m), 0.64–0.87 (2H, m), 0.83 (3H, d, J=6.5 Hz), 0.60 (3H, d, J=6.7 Hz), 0.29 (3H, d, J=6.6 Hz); Elemental analysis calculated for $C_{23}H_{35}NO_2FBr$: C, 60.52; H, 7.73; N, 3.07; found: C, 60.64; H, 7.87; N, 3.15; $[\alpha]_D^{25}$=−62.9° (c=1.0, methanol).

EXAMPLE 2

Preparation of (−)-menthyl (3S,4R)-trans-4-(4-fluorophenyl)-N-methylnipecotinate hydrobromide (1) in DBE and copper chloride A round bottom flask was charged with 4-fluorophenylmagnesium bromide (1M in THF, 56 mL, 0.0560 mol) and the flask was cooled to −3 to 1° C. and kept under a nitrogen atmosphere. To this mixture was added cuprous chloride (0.40 mg, 4.0 mmol) followed by (1R,2S,5R)-(−)-menthyl arecoline (11.2 g, 40.1 mmol) in DBE (total volume of solution=68 mL) over a 35 minute period. The cooling bath was removed and the solution was warmed to room temperature (23° C.) and the reaction was kept at this temperature a further 3 hours. It was then cooled to 10° C. and saturated aqueous ammonium chloride (55 mL) was added while maintaining the temperature below 17° C. The mixture was filtered through a Celite pad and the filter cake washed with DBE (1×10 mL) and the filtrate was transferred to a separatory funnel. The aqueous layer was removed and back-extracted with DBE (2×15 mL). The combined organic layers were concentrated to a weight of 51 g and cooled to −6° C. whereupon potassium tert-butoxide (1.95 g, 17.4 mmol) was added in portions over a 0.5 hour period. The reaction mixture was then stirred at 0° C. for about 3 hours and the pH was adjusted to 8.3 using 2.8% HCl at 0° C. and the reaction mixture transferred to a separatory funnel and the layers were separated. The aqueous layer was back-extracted with DBE (3×10 mL) and the organic layers were combined and concentrated to 58 g. This solution was cooled to −5° C. and 48% aqueous hydrobromic acid was added (6.69, 0.040 mol) over about 0.5 hours. The reaction mixture was charged with ethyl acetate (73 mL) and stirred at 0° C. for a further 1.5 hours. The precipitated product was collected by filtration and the filter cake was rinsed with a portion of ethyl acetate and the solid dried a 40 to 45° C. in vacuo. This provided 5.36 g (29.3% yield from (1R,2S,5R)-(−)-menthyl arecoline) of the (−)-menthyl (3S,4R)-trans-4-(4-fluorophenyl)-N-methylnipecotinate hydrobromide as a white solid and the material had the same $^1$H NMR as the product from example 1.

EXAMPLE 3

Preparation of (−)-menthyl (3S,4R)-trans-4-(4-fluorophenyl)-N-methylnipecotinate hydrobromide (1) in DBE, copper chloride and 30° C. Reaction Temperature for the Grignard Addition The same procedure as the one described in example 2 was followed except that the round bottom flask containing 4-fluorophenylmagnesium bromide (1M in THF, 56 mL, 0.0560 mol) and cuprous chloride (0.40 mg, 4.0 mmol) was maintained at 27–32° C. during the addition of the (1R,2S,5R)-(−)-menthyl arecoline substrate (30 minutes) and subsequent maintain time of 2 hours. The yield of (−)-menthyl (3S,4R)-trans-4-(4-fluorophenyl)-N-methylnipecotinate hydrobromide was 5.03 g (27.5% yield from (1R,2S,5R)-(−)-menthyl arecoline) and the material had the same $^1$H NMR as the product from example 1.

EXAMPLE 4

Preparation of (−)-menthyl (3S,4R)-trans-4-(4-fluorophenyl)-N-methylnipecotinate hydrobromide (1) in tetrahydrofuran (THF)

A round bottom flask is charged with 4-fluorophenylmagnesium bromide (1M in THF, 56 mL, 0.0560 mol) and the flask was cooled to −10 to −5° C. and kept under a nitrogen atmosphere. To this mixture was added a solution of (1R,2S,5R)-(−)-menthyl arecoline (11.2 g, 40.1 mmol) in THF (60 mL) over a 1.5 hour period. The cooling bath was removed and the solution was warmed to 15° C. and the reaction was kept at this temperature a further 8 hours. It was then quenched using saturated aqueous ammonium chloride (75 mL) while maintaining the temperature below 17° C. The mixture was filtered through a Celite pad and the filter cake washed with toluene (1×10 mL) and the filtrate was transferred to a separatory funnel. The aqueous layer was removed and back-extracted with toluene (2×50 mL). The combined organic layers were concentrated to a weight of 55 g and cooled to −5° C. whereupon potassium tert-butoxide (2.2 g, 19.6 mmol) was added in portions over a 0.5 hour period. The reaction mixture was then stirred at −3° C. for 3.7 hours and the pH was adjusted to 8 using 1.7% HCl at −5 to 0° C. and the reaction mixture transferred to a separatory funnel and the layers were separated. The aqueous layer was back-extracted with toluene (2×12 mL) and the organic layers were combined and concentrated to 24.9 g. This solution was cooled to to 0° C. and 48% aqueous hydrobromic acid was added (6.7, 0.040 mol) over about 0.5 hours. The reaction mixture was charged with ethyl acetate (36 mL) and stirred at 0° C. for a further 1.5 hours. This procedure was repeated another time with 48 mL of ethyl acetate and the reaction mixture stirred a further 3 hours. The precipitated product was collected by filtration and the filter cake was rinsed with a 12 mL portion of ethyl acetate and the solid dried a 50° C. in vacuo for 2 hours. This provided 5.2 g (28.5% yield from (1R,2S,5R)-(−)-menthyl arecoline) of (−)-menthyl (3S,4R)-trans-4-(4-fluorophenyl)-N-methylnipecotinate hydrobromide as a white solid and having the same $^1$H NMR as the product from example 1.

EXAMPLE 5

Preparation of (−)-menthyl (3S,4R)-trans-4-(4-fluorophenyl)-N-methylnipecotinate hydrobromide (1) in Heptanes/DBE and Addition of the Grignard reagent to the (1R,2S,5R)-(−)-menthyl arecoline substrate The same procedure as the one described in example 2 was followed except that cuprous chloride was not used and that the 4-fluorophenylmagnesium bromide (1M in THF, 56 mL, 0.0560 mol) reagent was added to a solution of (1R,2S,5R)-(−)-menthyl arecoline substrate (11.2 g, 0.040 mol) in DBE (total volume of solution=68 mL) and heptanes (42 mL) while maintaining the solution at −7 to −5° C. The yield of (−)-menthyl (3S,4R)-trans-4-(4-fluorophenyl)-N-methylnipecotinate hydrobromide was 5.94 g (32.5% yield from (1R,2S,5R)-(−)-menthyl arecoline) and the material had the same $^1$H NMR as the product from example 1.

EXAMPLE 6

Preparation of (−)-menthyl (3S,4R)-trans-4-(4-fluorophenyl)-N-methylnipecotinate hydrobromide (1) in toluene The same procedure as the one described in example 4 was followed except that the 4-fluorophenylmagnesium bromide (1M in THF, 56 mL, 0.0560 mol) reagent was added to a solution of (1R,2S,5R)-(−)-menthyl arecoline substrate (11.2 g, 0.040 mol) in toluene (60 mL) instead of THF. The yield of (−)-menthyl (3S,4R)-trans-4-(4-fluorophenyl)-N-methylnipecotinate hydrobromide was 5.35 g (29.3% yield from (1R,2S,5R)-(−)-menthyl arecoline) and the material had the same $^1$H NMR as the product from example 1.

EXAMPLE 7

Preparation of (−)-menthyl (3S,4R)-trans-4-(4-fluorophenyl)-N-methylnipecotinate hydrobromide (1) in dibutyl ether (DBE) and isolation of (3R,4S)-trans-4-(4-fluorophenyl)-N-methylnipecotinate hydrobromide (6)

The same procedure as the one described in example 1 was followed except that scale of the reaction was reduced by a factor of 2.5 [i.e., (1R,2S,5R)-(−)-menthyl arecoline=11.2 g versus 28.0 g). The yield of (−)-menthyl (3S,4R)-trans-4-(4-fluorophenyl)-N-methylnipecotinate hydrobromide was 6.0 g (33% yield from (1R,2S,5R)-(−)-menthyl arecoline) and the material had the same $^1$H NMR as the product from example. Elemental analysis calculated for $C_{23}H_{35}NO_2FBr$: C, 60.52; H, 7.73; N, 3.07; found: C, 60.64; H, 7.79; N, 3.25; $[\alpha]_D^{25}$=−64.8° (c=1.0, methanol).

The filtrate after isolation of 1 (77.83 g) was evaporated to 13.75 g and ethyl acetate (30 mL) was added and the resulting mixture stirred at ambient temperature. The precipitate was isolated by filtration to provide 3.1 g of 6 as a white solid. $^1$H NMR (DMSO) δ: 9.88 (1H, br.s), 7.14–7.25 (4H, m), 4.38 (1H, atd, J=4.1, 10.8 Hz), 3.71 (1H, ad, J=9.0 Hz), 3.53 (1H, ad, J=12.0 Hz), 3.14–3.25 (3H, m), 2.94–3.03 (1H, m), 2.86 (3H, ad, J=3.5 Hz), 1.91–2.09 (m, 2H), 1.51–1.55 (2H, m), 1.20–1.38 (1H, m), 1.04–1.20 (2H, m), 0.63–0.92 (2H, m), 0.77 (3H, d, J=7.0 Hz), 0.74 (3H, d, J=6.5 Hz), 0.55 (3H, d, J=6.8 Hz), 0.34 (1H, q, J=11.8 Hz); Elemental analysis calculated for $C_{23}H_{35}NO_2FBr$: C, 60.52; H, 7.73; N, 3.07; found: C, 60.79; H, 7.77; N, 3.03; $[\alpha]_D^{25}$=−4.8° (c=1.0, methanol).

EXAMPLE 8

Preparation of (−)-menthyl (3S,4R)-trans-4-(4-fluorophenyl)-N-methylnipecotinate hydrobromide (1) in dibutyl ether (DBE) and Cuprous Chloride (0.2 equivalents)

A round bottom flask was charged with a solution of (1R,2S,5R)-(−)-menthyl arecoline (44.2 g, 0.158 mol), DBE (300 mL) and cuprous chloride (3.13 g, 0.0317 mol, 0.2 eq) and the solution was cooled to 5° C. with stirring and under a nitrogen atmosphere. To this solution was added 4-fluorophenylmagnesium bromide (1M in THF, 205.7 mL, 0.2057 mol, 1.3 eq) over a 1 hour period while maintaining the reaction temperature below 11° C. The reaction was allowed to warm to room temperature and maintained a further 3 hours. The flask is cooled to 0 to 5° C. and saturated aqueous ammonium chloride (250 mL) was added while maintaining the temperature below 5° C. The mixture was filtered through a Celite pad and the filter cake washed with DBE (2×25 mL) and the filtrate was transferred to a separatory funnel. The aqueous layer was removed and back-extracted with DBE (50 mL). The combined organic layers were concentrated to 250 mL, dried over sodium sulfate and filtered. The filter cake was rinsed with dibutyl ether (2×25 mL) and the filtrate was cooled to 0 to 5° C. whereupon potassium tert-butoxide (14.21 g, 0.1266 mol, 0.8 eq) was added and the reaction mixture was stirred a further 1.5 hours until reaction completion. The reaction was then charged with water (200 mL) and the pH was adjusted to 8–9 using 32% HCl (10.8 g) and the reaction mixture transferred to a separatory funnel and the layers were separated. The aqueous layer was back-extracted with DBE (50 mL) and the organic layers were combined and concentrated to 150 mL. This solution was cooled to 0 to 5° C. and 48% aqueous hydrobromic acid was added (12.81 g, 0.1583 mol) over about 0.25 hours. The reaction mixture was charged with ethyl acetate (416 mL) and stirred at 0° C. for a further 3 hours. The precipitated product was collected by filtration and the filter cake was rinsed with two portion of ethyl acetate (50 mL) and the solid dried a 45° C. in vacuo. This provided 15.78 g (21.8% yield from (1R,2S,5R)-(−)-menthyl) arecoline) of the (−)-menthyl (3S,4R)-trans-4-(4-fluorophenyl)-N-methylnipecotinate hydrobromide as a white solid. HPLC purity=97.38% (by area); $[\alpha]_D^{25}=-65.52°$ (c=1.0, methanol).

The invention claimed is:

1. A process for the industrial scale preparation of a compound of structure A or salts thereof

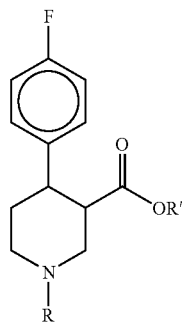

A in which R and R' are selected from alkyl, cycloalkyl, aryl, or aralkyl group, which comprises reacting a compound of structure B

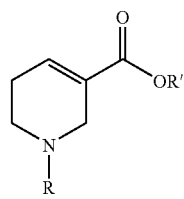

B with an organometallic compound of structure C,

C where X is Cl or Br, the reaction occurring in a suitable organic reaction solvent, selected from dibutyl ether wherein said reaction is in the complete absence of diethyl ether throughout the process wherein the resultant compound A is substantially free of a 1,2-conjugate by-product.

2. A process for the industrial scale preparation of a compound of structure A or salts thereof

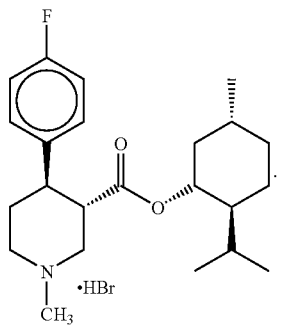

1 in which R and R' are selected from alkyl, cycloalkyl, aryl, or aralkyl group; which comprises reacting a compound of structure B

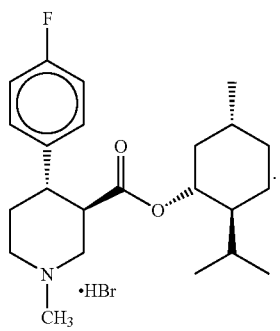

6 with an organometallic compound of structure C,

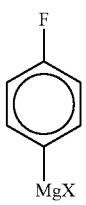

C where X is Cl or Br, the reaction occurring in a suitable organic reaction solvent wherein the reaction solvent is dibutyl ether and wherein in the preparation of Compound C diethylether is not present.

3. Process of claim 1 or 2 where R and R' are methyl.

4. Process of claim 1 or 2 where R is methyl and R' is (1R,2S,5R)-menthyl.

5. Process of claim 1 or 2 where X is Br.

6. Process of claim 1 or 2 where the salt form of A is HBr.

7. A process of claim 1 or 2 whereby the yield of A the 1,4-conjugated product is 50% or greater.

8. A process for the preparation of 1 according to the procedure of claim 1

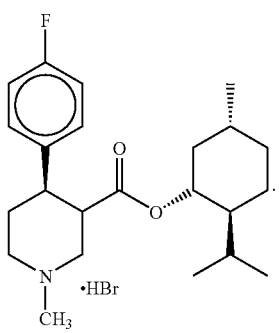

9. The process according to claim 8 where 1 is further converted to paroxetine hydrochloride.

10. A process for the preparation and isolation of 4 according to the procedure of claim 1 or 6

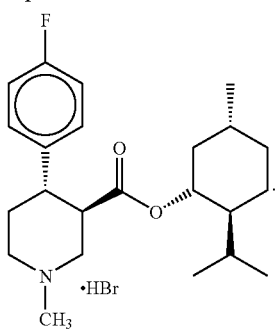

11. The process according to claim 10 where 6 is further converted to (+)-(3R,4S)-trans-3-[(1,3-Benzodioxol-5-yloxy)methyl]-4-(4-fluorophenyl)piperidine hydrochloride.

12. A method of preparing paroxetine, its salts, and ethers thereof comprising carrying out a process of any of claims 9 or 11.

13. A method of preparing paroxetine, its salts, and esters thereof comprising carrying out a process of any of claims 1–8 or 10 and further converting the product to paroxetine.

14. The method of claim 12 wherein the paroxetine formed is substantially crystalline.

15. The method of claim 13 wherein the paroxetine formed is substantially crystalline.

16. The method of claim 12 wherein the paroxetine formed is substantially amorphous.

17. The method of claim 13 wherein the paroxetine formed is substantially amorphous.

18. The process of any of claims 1–9 or 11 wherein the yield of the compound of structure A or salts thereof is greater than about 10%.

19. The process of claim 10 wherein the yield of the compound of structure A or salts thereof is greater than about 10%.

20. The process of claim 18 wherein the yield is greater than about 30%.

21. The process of claim 19 wherein the yield is greater than about 30%.

* * * * *